United States Patent [19]

Naftulin

[11] 4,437,472
[45] Mar. 20, 1984

[54] APPARATUS FOR COLLECTING FLUIDS

[76] Inventor: Henry Naftulin, 8341 N. Kenton Ave., Skokie, Ill. 60076

[21] Appl. No.: 428,143

[22] Filed: Sep. 29, 1982

Related U.S. Application Data

[63] Continuation-in-part of Ser. No. 275,498, Jun. 19, 1981, abandoned.

[51] Int. Cl.³ .................... A61B 5/00; B65D 33/00; B65D 81/00
[52] U.S. Cl. ................................ 128/767; 604/320; 604/408; 210/927
[58] Field of Search .................... 128/767; 604/4, 5, 6, 604/317, 319, 320, 322, 324, 403, 406, 408; 210/927

[56] References Cited

U.S. PATENT DOCUMENTS

| | | | |
|---|---|---|---|
| 3,929,133 | 12/1975 | Ragab | 604/319 |
| 4,060,107 | 11/1977 | Naftulin | 141/10 |
| 4,115,277 | 9/1978 | Swank | 210/927 |
| 4,129,131 | 12/1978 | Naftulin | 128/767 |
| 4,402,687 | 9/1983 | Denty | 604/319 |

Primary Examiner—William E. Kamm
Assistant Examiner—Deidre A. Foley
Attorney, Agent, or Firm—Dressler, Goldsmith, Shore, Sutker & Milnamow, Ltd.

[57] ABSTRACT

An improved flexible container for use in the collection and defibrination of blood. The flexible container is provided with an insitu filter associated with the outlet port. The fibrin filter includes a perforated inner tube extending into the outlet port and a reticulated foam insert secured around the inner tube. In accordance with one embodiment a perforated outer shell member encases the foam insert.

7 Claims, 5 Drawing Figures

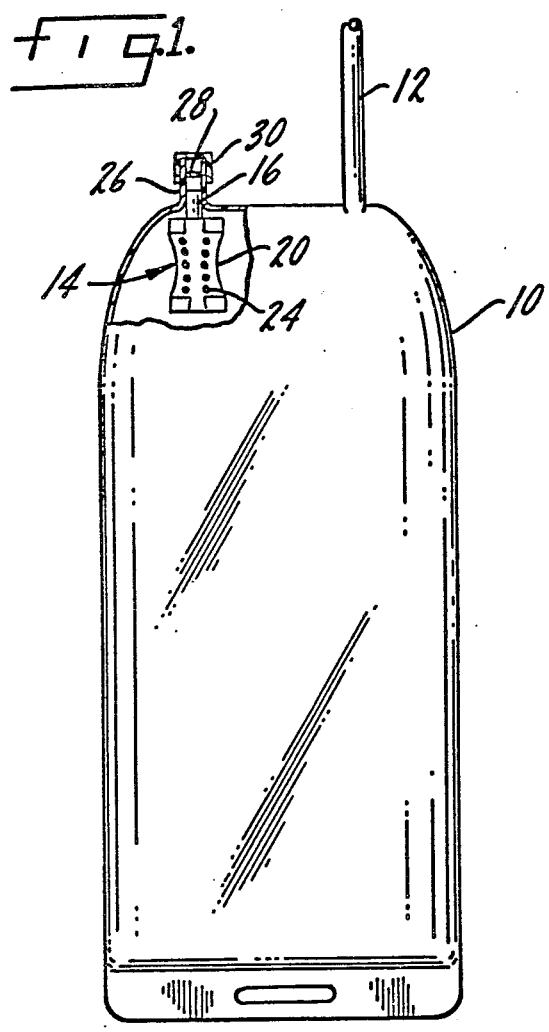
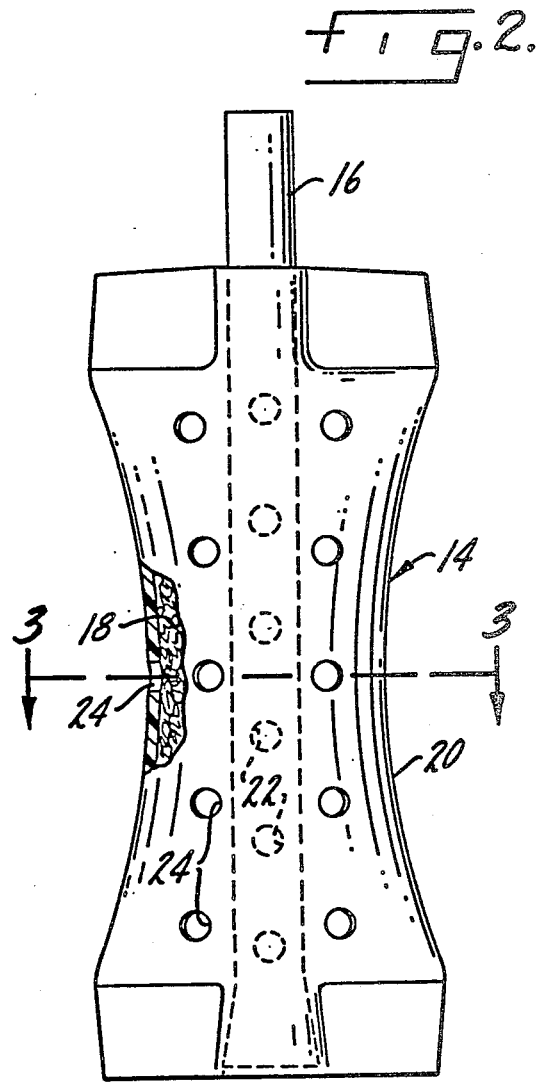
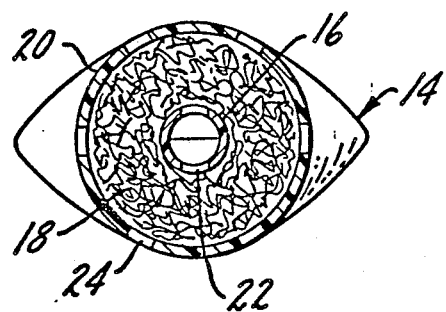

4,437,472

APPARATUS FOR COLLECTING FLUIDS

BACKGROUND OF THE INVENTION

This is a continuation-in-part of application Ser. No. 275,498, filed June 19, 1981 now abandoned.

This invention relates to an improved flexible container for use in the collection and defibrination of blood withdrawn from a human or other animal. More particularly, the flexible container of the present invention is particularly suitable for use in combination with the blood collection systems disclosed in U.S. Pat. Nos. 4,060,107 and 4,129,131, both patents having the same inventive entity as the present application.

In accordance with the systems described in the above patents, blood is collected in a flexible container having a quantity of glass beads or marbles or a reticulated material and a predetermined amount of gas placed therein. The flexible container is positioned within a rigid or semirigid inner chamber which is in turn positioned within an outer vacuum chamber. A vacuum of sufficient magnitude is drawn in the outer chamber, which expands the gas within the flexible container, so as to allow only approximately one-half of the flexible container to fill with blood upon performing the phlebotomy. The flexible container is sufficiently agitated, causing the glass beads to move rapidly through the blood or the blood to move through the reticulated material so as to whip out the fibrin.

Upon completion of the collection and defibration of the blood in the flexible container it is the usual practice to transfer or pool the collcted blood into a holding container. It has heretofore been the practice to transfer the blood through an outlet tube of the flexible container, having an external filter in communication therewith, for filtering out the fibrin which had previously been separated out of the blood. In performing such a tranasfer or pooling of the collected blood. It has been found that the outlet tube frequently becomes clogged with fibrin preventing the transfer of all of the blood in the flexible container.

SUMMARY OF THE INVENTION

It is a primary object of the present invention to provide a flexible container for collecting and defibrinating blood which permits the transfer of defibrinated blood therefrom without clogging the outlet port.

A further object is to provide a flexible container for collecting and defibrinating blood that assures the transfer of all of the defibrinated blood therefrom.

A still further object is to provide a flexible container for collecting and defibrinating blood which has an insitu fibrin filter associated with the outlet tube to reduce the risk of contamination when the blood is transferred therefrom.

In accordance with the present invention a flexible container is provided with an insitu fibrin filter associated with the outlet port. The fibrin filter includes a perforated inner tube extending into the outlet port and a reticulated foam insert secured around the inner tube. In one preferred embodiment a perforated outer shell member encases the foam insert.

BRIEF DESCRIPTION OF THE DRAWINGS

These and other objects and advantages of the invention will become apparent from the following description when taken in connection with the accompanying drawing. In the drawing, wherein like reference numerals have been used to designate like parts throughout:

FIG. 1 is a vertical elevational view of the flexible container of the present invention, partially broken away to show a first embodiment of the insitu fibrin filter:

FIG. 2 is an elevational view of the fibrin filter shown in FIG. 1, partially broken away to show internal details;

FIG. 3 is a sectional view taken along line 3—3 in FIG. 2.

DESCRIPTION OF A PREFERRED EMBODIMENT

Figure 4:
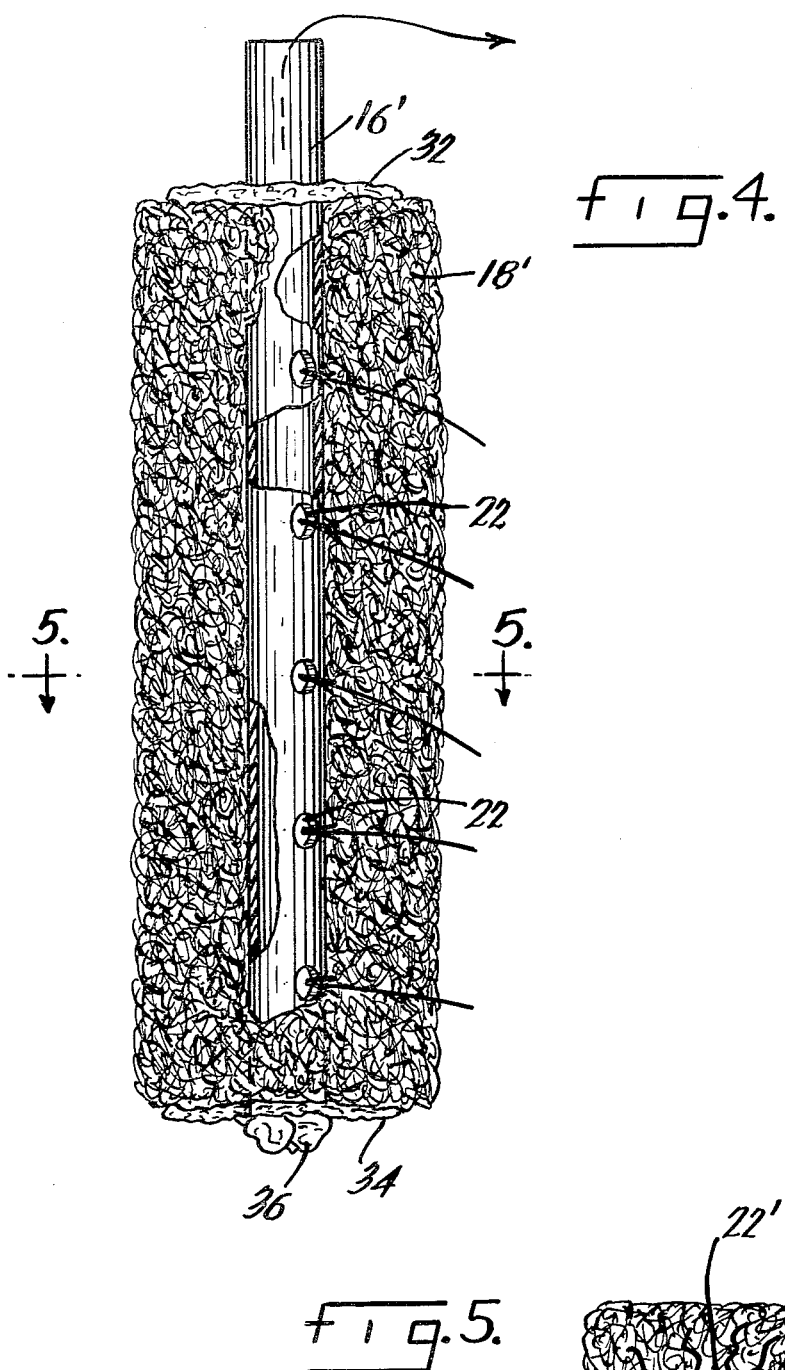
FIG. 4 is an elevational view of a second embodiment of the fibrin filter, partially broken away to show internal details.

The present invention is hereinbelow described as being used in combination with the method and apparatus disclosed in U.S. Pat. No. 4,129,131. The disclosure of this patent is hereby incorporated by reference for the purpose of providing minor structural details of a flexible container of the type which utilizes the present invention. The disclosure of the present invention in combination with a specific blood collection system should not be construed as meaning that the teachings of the present invention are limited to the use with a specific blood collection system.

Referring to FIGS. 1-3, the blood collecting flexible container of the present invention is indicated generally at 10. The skin portion of container 10 is of conventional construction and may be made from many flexible materials well known in the art, the most commonly used type being manufactured from a plastic material such as a polyvinylchloride resin base material. Container 10 includes a blood collection line 12 having one end in communication with the interior of container 10 and the other end adapted for receipt of the collected blood thereinto. As specifically disclosed in U.S. Pat. No. 4,129,131, a sufficient quantity of glass beads, marbles, metallic balls or formed elements, or a reticulated foam material, may be sealed within container 10 along with a predetermined amount of gas.

In accordance with a first embodiment of the present invention, an insitu fibrin filter assembly, indicated generally at 14, is positioned within container 10. Filter assembly 14 includes a perforated inner tube 16, a reticulated foam insert 18, and a perforated outer shell member 20.

Inner tube 16 is formed with a plurality of openings 22 therein, which extend over the major extent of the tube. Insert 18 is made from a reticulated material, such as a urethane foam, and has a central hole formed therein for receipt of tube 16 therethrough. The present invention contemplates the use of such a material having in the range of 5-70 pores per linear inch and preferably about 10 pores per linear inch. The outer shell member 20, which encases the insert 18, is made from a flexible material, such a polyvinylchloride, and has a plurality of openings 24 formed therein. Shell 20 is positioned around insert 18 and crimped and sealed at its lower end along with tube 16, so as to close off the lower end of tube 16, and sealed at its upper end around tube 16, so as to permit blood flow through the upper end of tube 16. The upper end of tube 16, having no openings 22 therethrough, extends upward into the outlet port 26 of container 10. A diaphragm 28 is provided above the end of tube 16 in outlet port 26. A port cap 30 closes off outlet port 26.

In operation, blood is collected into container 10 and the fibrin is separated therefrom within the container preferably in the manner as is fully disclosed in U.S. Pat. No. 4,129,131. It is the usual procedure to then transfer the defibrinated blood to a holding container where it is retained for future use. In accordance with the present invention, the port cap 30 is removed from outlet port 26 and an auxiliary transfer line is secured to port 26 after the diaphragm 28 is punctured so as to permit blood flow from container 10 through the transfer line. The other end of the transfer line is in communication with the holding container. In order to facilitate the gravity flow of blood from container 10 into the holding container, the container 10 is turned upside down and supported at an elevation above the holding container. As the blood flow from container 10 it passes through the openings 24 in shell 20 into the filter assembly 10. As the blood passes through the reticulated material 18, the fibrin which had previously been separated from the blood is filtered out and retained in material 18. The fibrin free blood then passes through the openings 22 and into tube 16, whereupon it passes through tube 16 into the transfer line for passage to the holding container.

Figure 5:
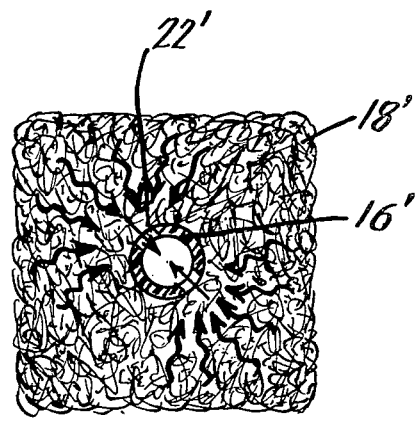
FIG. 5 is a sectional view taken along line 5—5 in FIG. 4.

Referring to FIGS. 4 and 5, a second embodiment of the fibrin filter assembly is indicated generally at 14'. Filter assembly 14' is similar in construction and operation to filter assembly 14, the differences being in the manner in which the foam insert 18 is secured to the perforated inner tube 16 without the use of the outer shell member 20.

Filter assembly 14' includes a perforated inner tube 16' and a reticulated foam insert 18'. Inner tube 16' and reticulated foam insert 18' are constructed and positioned as discussed with regards to their counterparts in filter assembly 14. However, in this embodiment the upper and lower ends of the foam insert 18' are permanently secured to upper and lower portions of the inner tube 16'. In accordance with a preferred form of this embodiment, a pair of vinyl collars (not specifically shown) are positioned on inner tube 16', respectively immediately above and below the perforated portions of inner tube 16'. The foam insert 18' is positioned around the inner tube 16' between these two collars. The vinyl collars are then fused to the inner tube 16' and the foam insert 18', as indicated at 32 and 34. At the same time, the lower end of inner tube 16' is sealed, as indicated at 36. In so doing, the foam insert 18' is permanently secured to the vinyl collars which in turn are permanently secured to the inner tube 16', at 32 and 34. Accordingly, the foam insert 18' is affixed to inner tube 16' in a manner which assures that all of the blood which is transferred from the container 10 must pass through the foam insert 18' before entering into inner tube 16'. By use of well known radio frequency fusing techniques the fusion of the collars to the inner tube 16' and the foam insert 18' and the sealing off of the lower end of inner tube 16' may be accomplished at the same time.

The flexible container of the present invention, and the insitu fibrin filter associated therewith, offers many advantages over theretofore used containers. The fibrin is collected internally within the fibrin filter 10 and eliminates the problem of the fibrin clogging up the outlet port. This assures that all of the blood is transferred from the collection container and eliminates the necessity of an operator constantly monitoring for interruptions in blood flow. It is not necessary for the operator to have to secure an external fibrin filter into the transfer line. The present invention also permits the simultaneous pooling of the blood from a plurality of collection containers into a single holding container. Further, the entire system may be sterilized as an integral unit which reduces the likelihood of contamination of the blood.

This invention is not to be limited by the embodiment shown in the drawing and described in the description, which are given by way of example and not of limitation, but only in accordance with the scope of the appended claims.

What is claimed is:

1. In combination with a flexible container used to collect and defibrinate blood therein, an insitu fibrin filter means positioned within said container and in communication with the outlet port of said container for collecting fibrin prior to its entry into said outlet port, comprising: a perforated inner tube member having an upper end extending into said outlet port, and a lower end extending into said container; and reticulated foam insert secured around said inner tube member, said inner tube member being sealed at its other end so as to preclude the entry of blood thereinto.

2. The invention as defined in claim 1 wherein said reticulated foam insert has in the range of 5-70 pores per linear inch.

3. The invention as defined in claim 1 wherein the upper end of said inner tube member terminates inside said outlet port.

4. The invention as defined in claim 3 wherein a diaphragm means closes off said outlet port outside of the upper end of said inner tube member.

5. The invention as defined in claim 1 wherein the portion of said inner tube which extends outside of said foam insert is not perforated.

6. The invention as defined in claim 1 further including a perforated outer shell member encasing said foam insert, said outer being sealed at its respective ends around said inner tube member.

7. The invention as defined in claim 5 wherein the upper and lower ends of said foam insert are secured to respective upper and lower portions of said inner tube member.

* * * * *